United States Patent [19]

Nakatsuka et al.

[11] Patent Number: 4,945,162
[45] Date of Patent: Jul. 31, 1990

[54] NOVEL RADIOACTIVE PROPYL 2-IODOSPIROPERIDOL AND PROCESSES FOR THE PREPARATION THEREOF

[75] Inventors: Iwao Nakatsuka, Kobe; Masami Okuno, Osaka, both of Japan

[73] Assignee: Sumitomo Chemical Company, Limited, Osaka, Japan

[21] Appl. No.: 128,821

[22] Filed: Dec. 4, 1987

[30] Foreign Application Priority Data

Dec. 26, 1986 [JP] Japan ................... 61-314256

[51] Int. Cl.$^5$ .......................................... C07D 471/10
[52] U.S. Cl. ................................................... 546/20
[58] Field of Search ............................................ 546/20

[56] References Cited

U.S. PATENT DOCUMENTS

| 3,155,669 | 11/1964 | Janssen | 546/20 |
|---|---|---|---|
| 3,238,216 | 3/1966 | Janssen | 546/20 |
| 3,890,323 | 6/1975 | Yamamoto et al. | 546/20 |
| 3,979,390 | 9/1976 | Sasajima et al. | 546/20 |
| 4,687,852 | 8/1987 | Nakatsuka et al. | 546/20 |
| 4,739,060 | 4/1988 | Saji et al. | 548/20 |

FOREIGN PATENT DOCUMENTS

| 253507 | 4/1967 | Austria | 546/20 |
|---|---|---|---|
| 48-92378 | 11/1973 | Japan | 546/20 |
| 49-14476 | 2/1974 | Japan | 546/20 |
| 49-24973 | 3/1974 | Japan | 546/20 |
| 50-53845 | 1/1975 | Japan | 546/20 |
| 59-95288 | 6/1984 | Japan | 546/20 |
| 62-48684 | of 1987 | Japan | 546/20 |
| 2155473 | 9/1985 | United Kingdom | 546/20 |

OTHER PUBLICATIONS

Glowinski et al: "J. of Neurochemistry" (1966), vol. 13, pp. 655–669.
Chemical Abstracts, vol. 95, No. 11, Sep. 14, 1981, p. 6, Abstract 90682n.
Chemical Abstracts, vol. 99, No. 23, Dec. 5, 1983, p. 392, Abstract 190706z.

*Primary Examiner*—Robert T. Bond
*Attorney, Agent, or Firm*—Stevens, Davis, Miller & Mosher

[57] ABSTRACT

A radioactive propyl 2-iodospiroperidol of the formula:

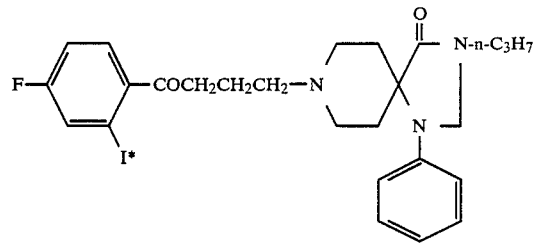

wherein I* is a radioactive iodine atom. The radioactive compound has a high affinity for dopamine receptors and is very useful as a radioactive diagnostic agent and as a radiopharmaceutical.

2 Claims, No Drawings

NOVEL RADIOACTIVE PROPYL 2-IODOSPIROPERIDOL AND PROCESSES FOR THE PREPARATION THEREOF

This invention relates to a novel radioactive propyl 2-iodospiroperidol (hereinafter referred to as PISP) of the formula:

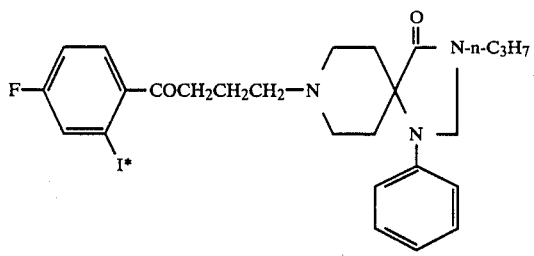

wherein I* is a radioactive iodine atom, and processes for producing the same.

The compound of this invention is a novel compound not disclosed in any literature. The compound of this invention has a higher affinity for dopamine receptors than the other known iodinated analogues such as 2-iodospiroperidol (hereinafter referred to as 2-ISP) and methyl 2-iodospiroperidol (hereinafter referred to as MISP), which have been disclosed in U.S. Pat. No. 4,687,852 and in Japanese Patent Application Kokai (Laid-Open) No. 62-48684 (See Example 4).

Another characteristic of the compound of this invention is its considerably high retention in the corpus striatum in mouse. Therefore, the compound of this invention is very useful as a radioactive diagnostic agent and as a radiopharmaceutical.

The radioactive propyl 2-iodospiroperidol (I) produced by this invention permits quantitative measurement of dopamine receptors in the living human brain by applying a suitable method such as a probe method, a single photon emission computed tomography (SPECT) method, and the like. Therefore, a certain neuropsychiatic disorder caused by abnormality of dopamine receptor concentration can be diagnosed by using above system. The compound of this invention can also be used as a standard material for evaluation in vivo of dopamine receptor specific drugs, and it is useful for the diagnosis and treatment of other diseases, such as breast cancer, resulting from a change of dopamine receptors. Furthermore, the compound of this invention can be used as a radioactive ligand in the various kinds of in vitro radioassays such as RIA, RRA and the like.

The method for the preparation of the compound of this invention will be described below.

The compound of this invention of the abovementioned formula (I) can be produced by a conventional method for the synthesis of radioactive iodine compounds. For instance, it can be produced according to either Process A or Process B shown below.

Process A

A radioactive 2-ISP of the formula (II):

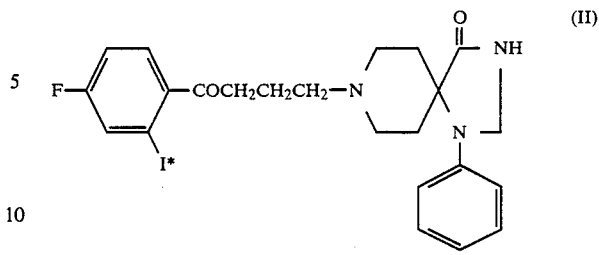

wherein I* is the same as described above, which is disclosed in U.S. Pat. No. 4,687,852 is reacted with 1-iodopropane in a solvent in the presence of a base, if necessary, in the presence of a crown-ether or a phase transfer catalyst, at a temperature of 30° to 100° C. As the solvent described above, for example, acetone, methyl ethyl ketone, methylene chloride, dichloroethane, ether, isopropyl ether, tetrahydrofuran, dioxane, benzene, acetonitrile, water and a mixture of these solvents are exemplified. And as the base, for example, a caustic alkali, an alkali metal, an alkali metal hydride and a quaternary amine compound are exemplified.

Process B

A halogeno compound of the formula:

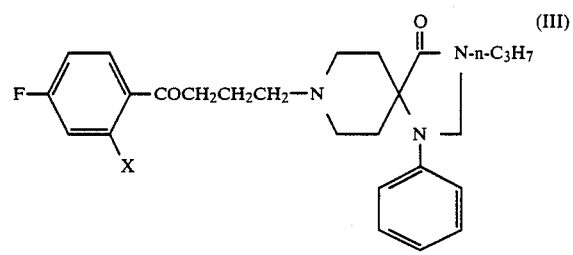

wherein X is a halogen atom is subjected to an exchange reaction with a radioactive metal iodide in a solvent at a temperature of 50° to 180° C. As the solvent described above, for example, acetonitrile, dimethylformamide, ethylene glycol, an ether derivative of ethylene glycol, an ether derivative of diethylene glycol, water and the like are exemplified.

The compound (I) obtained can be purified by a conventional method such as thin layer chromatography (TLC) or high-performance liquid chromatography (HPLC).

In the process of this invention, for example, I-123, I-125, I-131, I-132, etc. are exemplified as the radioactive iodine atom, and I-123 is preferred. The radioactive metal iodide means a metal salt of the above radioactive iodine, and may be any of those capable of providing a radioactive I- ion, though alkali metal salts such as, for example, sodium iodide, potassium iodide and lithium iodide are preferred. As the halogen ion in the formula (III), anions of chlorine, bromine, iodine and the like are exemplified.

The present invention will further be specifically described below referring to Examples.

EXAMPLE 1

Preparation of
8-[4-(4-fluoro-2-iodophenyl)-4-oxobutyl]-3-propyl-1-phenyl-1,3,8-triazaspiro[4.5]decan-4-one
(propyl-2-iodospiroperidol).

1-Iodopropane (20 mg) and tetra-n-butylammonium hydroxide (8 ml) were added to 2-iodospiroperidol (521 mg), and the mixture was stirred at a temperature of 40° to 50° C. for an hour. After cooling the same, water was added to the reaction mixture and the mixture was subjected to an extraction by chloroform. Then the solvent was removed by distillation to obtain a crude product. This was purified by silica gel column chromatography to obtain propyl 2-iodospiroperidol (420 mg).

IR(CHCl$_3$)cm$^{-1}$: 1705 (C=O).

$^1$H-NMR(CDCl$_3$) δ(ppm): 0.95 (3H, t, J=7 Hz, CH$_3$), 1.40–3.00 (16H, m, —CH$_2$—), 3.30 (2H, t, J=7 Hz, N—CH$_2$—), 4.60 (2H, s,

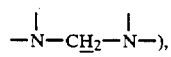

6.80–7.70 (8H, m, benzene ring H).

Mass spectrum (70 eV) m/e: 563 [M+], 286 (base peak).

EXAMPLE 2

Preparation of
[$^{125}$I]-8-[4-(4-fluoro-2-iodophenyl)-4-oxobutyl-3-propyl-1-phenyl-1,3,8-triazaspiro[4.5]decan-4-one
([$^{125}$I]-PISP).

1-Iodopropane (100 μl) and tetra-n-butylammonium hydroxide (30 μl) were added to an aqueous solution of [$^{125}$I]-2-ISP (500 μCi). The mixture was stirred at room temperature for an hour. The resulting crude product was purified by HPLC (column; Licrosorb ® RP-18, solvent: water/methanol/acetonitrile/triethylamine=164/336/68/0.2 to obtain [$^{125}$I]-PISP (400 μCi). This product was identical with the specimen obtained in the Example 1 in Rf values of TLC and HPLC.

EXAMPLE 3

Preparation of [$^{123}$I]-PISP

In the same manner as in Example 2, [$^{123}$I]-PISP (156 μCi) was obtained from [$^{123}$I]-2-ISP (200 μCi).

EXAMPLE 4

PISP, 2-ISP and MISP were screened as for the dopamine receptor binding affinity according to the method reported by Hamblin [Biochem. Pharmacol. 33, 877–887 (1984)]. An aliquot of striatal membrane preparations was incubated at 23° C. for 30 minutes with each of the unlabeled competing drugs (PISP, 2-ISP and MISP) in different concentration, ketanserine and $^3$H-spiroperidol (hereinafter referred to as $^3$H-SP). The incubation was terminated by adding ice-cold TEAN buffer followed by a rapid filtration through a Whatman GF/B filter. The bound $^3$H-SP retained on the filter was extracted with ACS II (Amersham) and counted. All incubations were done in triplicate. Nonspecific binding was determined in tubes containing (+)butaclamol. Specific binding was calculated by subtracting the nonspecific binding from the total binding. IC$_{50}$ values, the concentrations of the tested compounds that cause 50% inhibition of the specific $^3$H-SP binding, were assessed using from six to eight samples at different concentrations, in triplicate.

The results were summarized in Table 1.

TABLE 1

Inhibitory Potency (Affinity for Dopamine Receptors) of Iodinated Butyrophenones For $^3$H-SP to Rat Striatal Membranes

| Compound | IC$_{50}$ (M) | Ki (M) | Relative Potency |
| --- | --- | --- | --- |
| 2-ISP | $1.1 \times 10^{-8}$ | $1.0 \times 10^{-9}$ | 100 |
| MISP | $5.5 \times 10^{-8}$ | $5.0 \times 10^{-9}$ | 20 |
| PISP | $2.5 \times 10^{-9}$ | $0.2 \times 10^{-9}$ | 500 |

What is claimed is:

1. A radioactive propyl 2-iodospiroperidol of the formula:

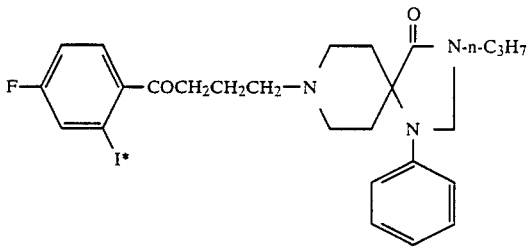

wherein I* is radioactive iodine atom.

2. The compound according to claim 1, wherein I* is an atom selected from the group of iodine isomers consisting of I-123, I-125, I-131 and I-132.